(12) United States Patent
Maillart et al.

(10) Patent No.: US 10,302,533 B2
(45) Date of Patent: May 28, 2019

(54) FLUID SAMPLE ANALYSIS SYSTEM AND METHOD FOR TRANSFERRING A FLUID SAMPLE IN A FLUID CELL USING TWO-WAY CIRCULATION

(71) Applicant: HORIBA JOBIN YVON SAS, Longjumeau (FR)

(72) Inventors: Emmanuel Maillart, Massy (FR); Cecile Lerondeau, Gif sur Yvette (FR); Geraldine Melizzi, Les Ulis (FR); Didier-Luc Brunet, Brunoy (FR); Denis Cattelan, Antony (FR)

(73) Assignee: HORIBA JOBIN YVON SAS, Longjumeau (FR)

( * ) Notice: Subject to any disclaimer, the term of this patent is extended or adjusted under 35 U.S.C. 154(b) by 22 days.

(21) Appl. No.: 15/120,358

(22) PCT Filed: Feb. 19, 2015

(86) PCT No.: PCT/FR2015/050406
§ 371 (c)(1),
(2) Date: Aug. 19, 2016

(87) PCT Pub. No.: WO2015/124873
PCT Pub. Date: Aug. 27, 2015

(65) Prior Publication Data
US 2017/0067805 A1    Mar. 9, 2017

(30) Foreign Application Priority Data

Feb. 21, 2014  (FR) ..................................... 14 51411

(51) Int. Cl.
*G01N 1/38*         (2006.01)
*G01N 35/08*     (2006.01)
(Continued)

(52) U.S. Cl.
CPC ............. *G01N 1/38* (2013.01); *G01N 21/658* (2013.01); *G01N 35/08* (2013.01); *G01N 35/1095* (2013.01); *G01N 35/1097* (2013.01)

(58) Field of Classification Search
CPC ........ G01N 1/38; G01N 21/658; G01N 35/08; G01N 35/1097; G01N 35/1095
See application file for complete search history.

(56) References Cited

U.S. PATENT DOCUMENTS 5,756,905 A * 5/1998 Ueda ...................... G01N 30/18
                                                                  73/864.24
7,175,812 B2 * 2/2007 Tatsumi .................. B01L 3/021
                                                                    422/510
(Continued)

FOREIGN PATENT DOCUMENTS

JP    2006/242912 A    9/2006
WO     03/025547 A1    3/2003
(Continued)

OTHER PUBLICATIONS

International Search Report, dated May 29, 2015, from corresponding PCT application.

*Primary Examiner* — Michael P LaPage
(74) *Attorney, Agent, or Firm* — Young & Thompson

(57) ABSTRACT

A system for transferring a fluid sample in a fluid cell, includes a first and a second fluid circuit connected, respectively, to a first and a second inlet-outlet (1, 2) of a fluid cell (10), first injection elements (80) configured so as to inject, in series, into the first fluid circuit (11, 12, 13): a buffer solution, a first separation fluid volume followed by a fluid sample, then a second separation fluid volume and another buffer solution. The system includes first discharge elements arranged on the first fluid circuit near the first inlet-outlet (1), second injection elements (90, 91) arranged on the second fluid circuit (21, 22, 23) near the second inlet-outlet (2), and (Continued)

Figure 6:
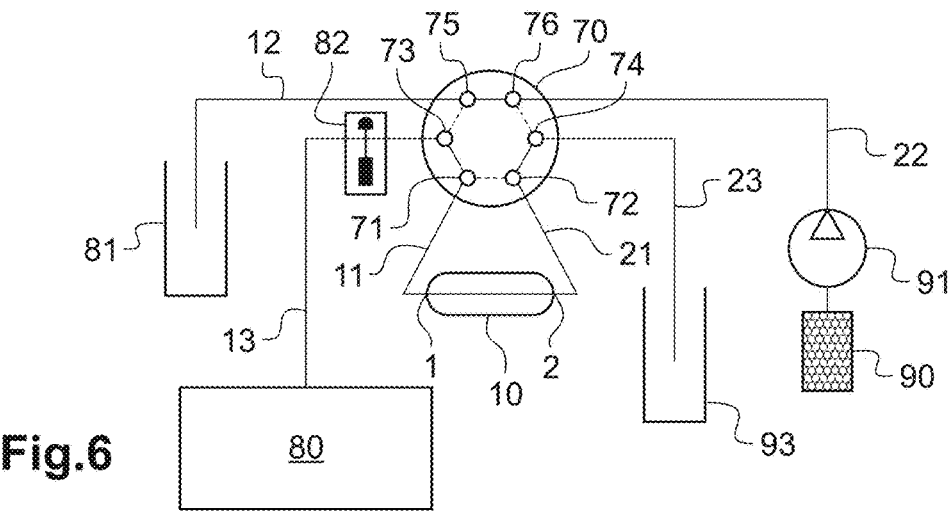

two-way circulation elements configured so as to circulate the fluid sample in two opposite directions in the fluid cell (10) without the passage of separation fluid into the fluid cell (10).

9 Claims, 5 Drawing Sheets

(51) Int. Cl.
   *G01N 21/65* (2006.01)
   *G01N 35/10* (2006.01)

(56) References Cited

U.S. PATENT DOCUMENTS

| | | | |
|---|---|---|---|
| 8,004,669 | B1 | 8/2011 | Kim et al. |
| 2002/0170365 | A1* | 11/2002 | Sklar .................. G01N 15/1459 73/865.5 |
| 2003/0040105 | A1* | 2/2003 | Sklar .................. B01F 13/0071 435/287.2 |
| 2005/0250145 | A1 | 11/2005 | Hirabayashi et al. |
| 2010/0196205 | A1* | 8/2010 | Quinn ................ G01N 35/1095 422/82 |
| 2010/0197512 | A1* | 8/2010 | Trinkle .................. G01N 35/08 506/7 |
| 2011/0052446 | A1 | 3/2011 | Hirano et al. |
| 2011/0295512 | A1* | 12/2011 | Quinn .................... G01N 35/08 702/19 |
| 2015/0045729 | A1* | 2/2015 | Denzer .................. A61M 5/20 604/110 |

FOREIGN PATENT DOCUMENTS

| | | |
|---|---|---|
| WO | 2012/045325 A1 | 4/2012 |
| WO | 2014/191022 A1 | 12/2014 |

* cited by examiner

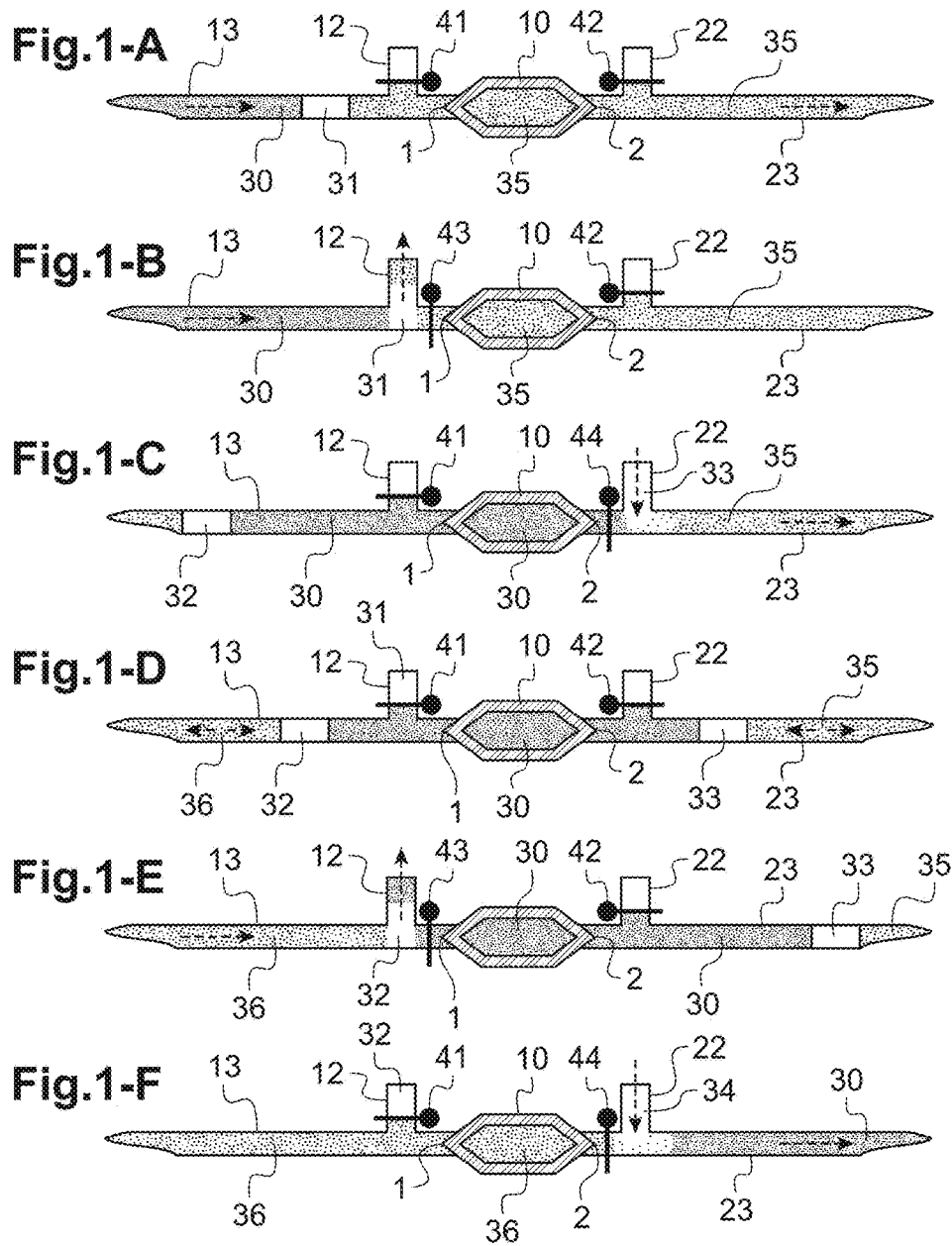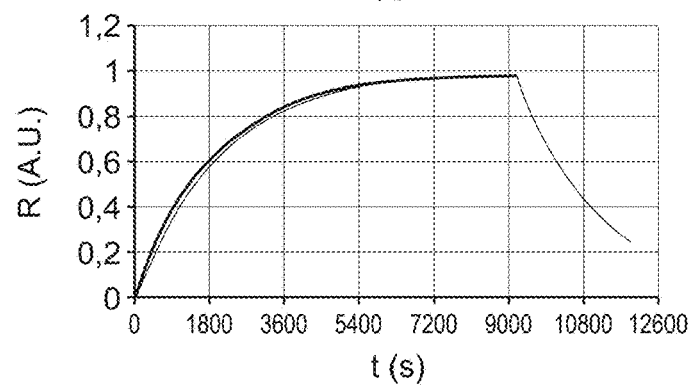

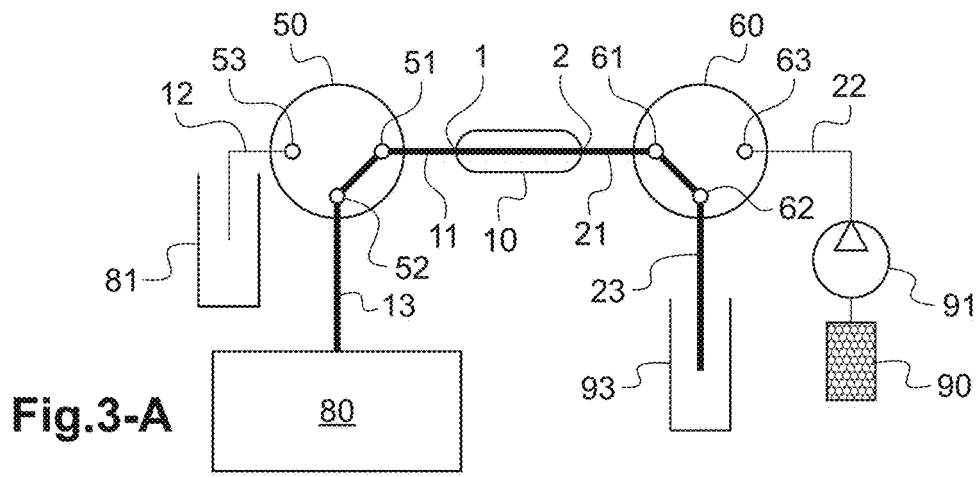
Fig.3-A
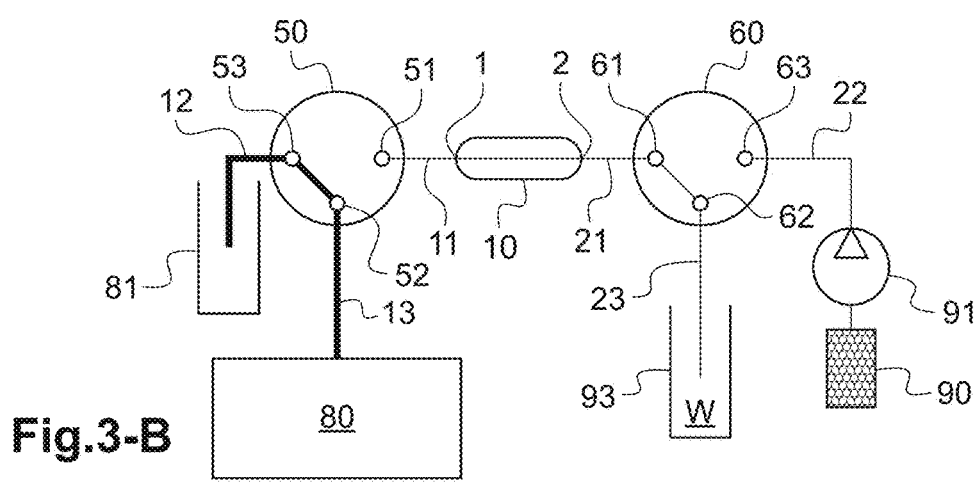
Fig.3-B
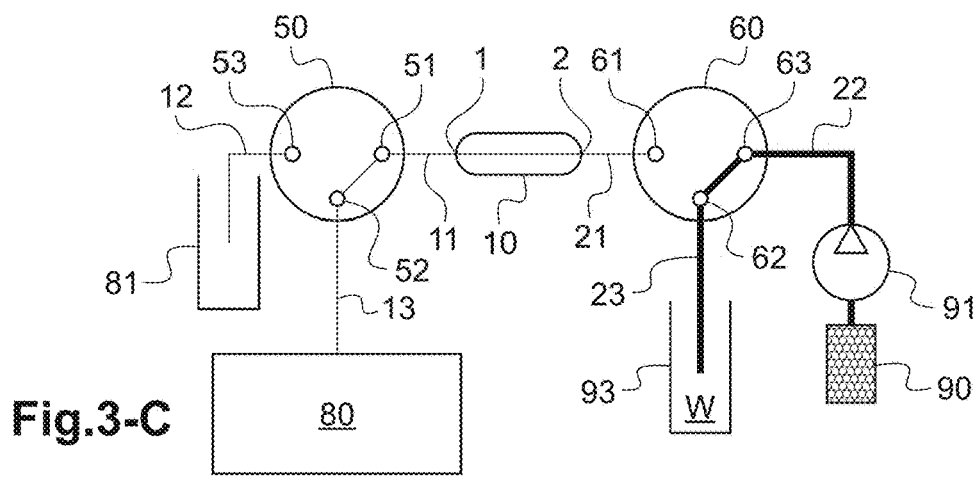
Fig.3-C

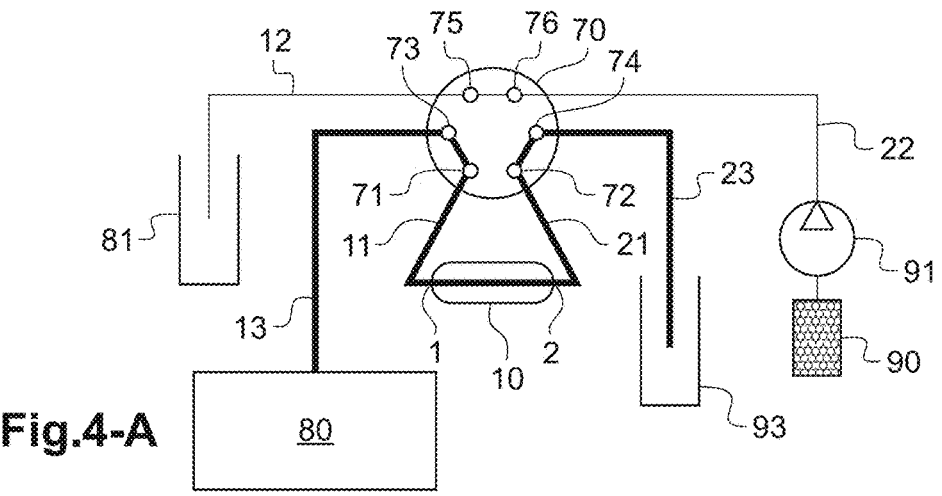
Fig.4-A
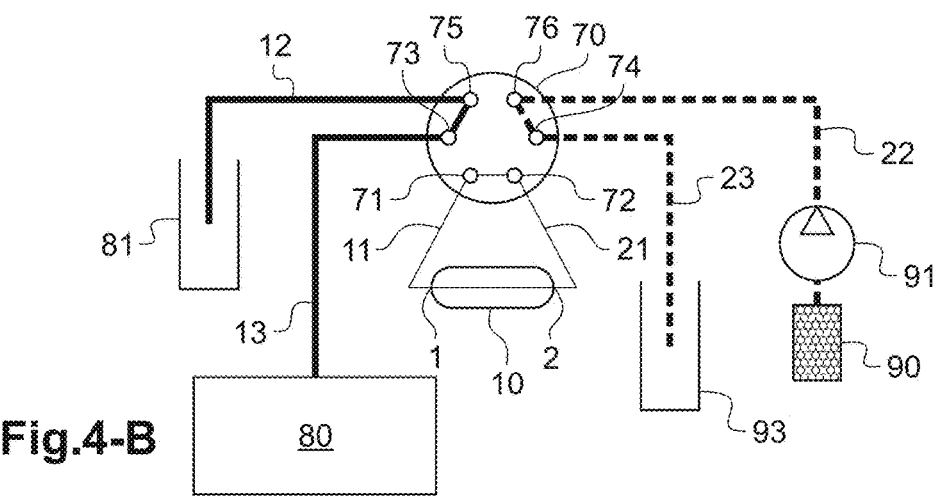
Fig.4-B
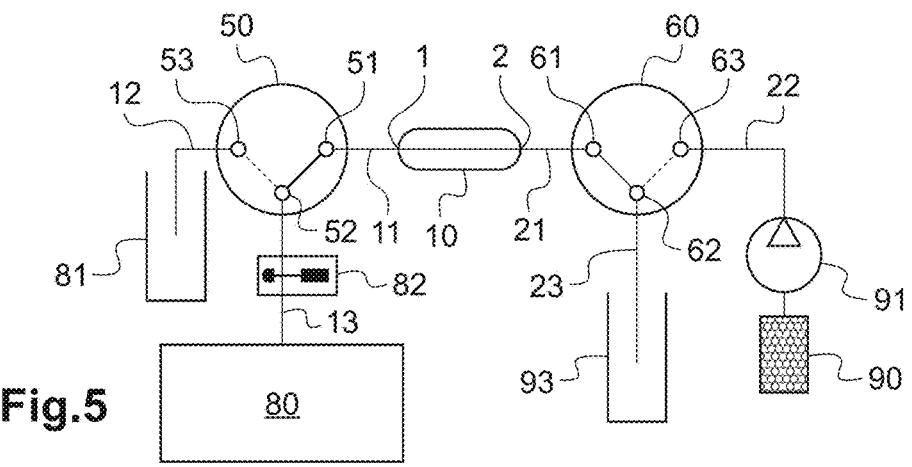
Fig.5

FLUID SAMPLE ANALYSIS SYSTEM AND METHOD FOR TRANSFERRING A FLUID SAMPLE IN A FLUID CELL USING TWO-WAY CIRCULATION

TECHNICAL FIELD OF THE INVENTION

This invention relates to a system for transferring a fluid sample to a fluid cell for analysis of said sample and for the transfer of said fluid sample from the fluid cell, after analysis.

The invention applies in particular to devices for measuring biological interactions and biosensors.

TECHNICAL BACKGROUND

In general, the, the fluid sample analysis technique most commonly used is liquid phase chromatography (HPLC) in which the fluid samples are sent to a column.

Other fluid sample analysis systems are provided with a fluid cell configured for analysis of interactions between the fluid sample and molecules. In these systems, a fluid sample is collected, in general a small quantity, the fluid sample is transferred to a fluid cell where an analysis is performed, then the fluid sample is extracted from the fluid cell.

In this document, by sample we mean a fluid sample coming from a liquid source (for example a physiological liquid) or a preparation in solution, for example by dissolution of a component in a solvent.

Preferably, a fluid cell is configured so as to enable an analysis of the sample by an optical analysis technique. More specifically, the interaction between a sample and a surface of the fluid cell is analyzed by optical means implementing evanescent optical phenomena, such as, for example: surface plasmon resonance (SPR), but also other types of plasmons such as localized plasmons (LSPR for localized surface plasmon resonance) or long range plasmons (LRSPR for long range surface plasmon resonance), resonant mirrors, waveguides or Bloch surface waves (BSW).

Advantageously, the fluid cell comprises a biochip or a biosensor including a functionalized surface for enabling the simultaneous interaction and analysis of a sample on a matrix of interaction sites, the different interaction sites being dedicated to the interaction with different molecules or particular reagents.

In a biosensor, the signal that measures the interaction between an analyte and the biosensor is linked to the concentration of the sample to be analyzed as well as to the duration of the interaction.

Thus, in the simple case of an interaction between a ligand L immobilized on a biochip and an analyte A in solution capable of interacting according to a stoichiometry of one to one, the chemical reaction is written:

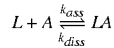

where $k_{ass}$ represents the association rate constant of the reaction in $M^{-1}s^{-1}$ and $k_{diss}$ represents the dissociation rate constant of the reaction in $s^{-1}$.

The response R(t) of the biosensor to this reaction may be written in the form of the following equation:

$$R(t) = \frac{[A] \cdot R_{max}}{[A] + K_D} \cdot \left(1 - e^{-(k_{ass} \cdot [A] + k_{diss}) \cdot t}\right)$$

where $R_{max}$ represents the saturation response of the biosensor, $K_D$ ($=k_{diss}/k_{ass}$) represents the dissociation constant of the reaction in M, [A] represents the analyte concentration of the sample and t represents the time.

The higher the concentration of the sample is and the stronger the measured signal is, as long as the biochip recognition elements are not saturated. The longer the duration of the passage of the sample into the fluid cell is, the longer the duration of the interaction is and the stronger the measured signal is, as long as the recognition reaction has not reached its equilibrium.

It is sought to improve the sensitivity of a fluid analysis system, for example for the analysis of samples low in concentration and/or low in quantity. There are solutions for increasing the time of passage of a sample into a fluid cell without increasing the consumption of said sample.

A solution consists in implementing a closed-circuit recirculation system, the outlet of the fluid cell being connected to the inlet of the fluid cell. The advantage of a closed-circuit recirculation is that the diffusion of the sample is prevented regardless of the duration of the passage of the sample into the fluid cell. However, the volume of sample in recirculation is equal to the volume of the closed circuit. For certain samples, the available volume may be very low and lower than the volume of the closed circuit. For another sample, it may be necessary to circulate, in a loop, a larger volume of a low-concentration sample in order for the number of molecules having interacted on the biochip to remain negligible with respect to the total quantity of said molecule in the sample. Thus, the concentration of sample remains constant over the time of passage into the fluid cell, by elimination of the depletion phenomenon.

Another solution uses a two-way system, the direction of circulation of the sample in the fluid cell being periodically reversed: the outlet of the fluid cell periodically becomes the inlet, and vice versa. The two-way system is compatible with different sample volumes and different sample concentrations.

In addition, the sample to be analyzed generally comprises a solution and target molecules to be detected via a biosensor. In general, the sample to be analyzed is injected after a reference liquid, of the buffer solution type, such as PBS (phosphate buffer saline) or HBS (HEPES buffer solution, with HEPES for 4-(2-hydroxyethyl)-1-piperazine ethane sulfonic acid), not containing target molecules. During the transfer of the sample to the fluid cell, the sample has a tendency to be diluted by diffusion in contact with the buffer solution, which reduces its mean concentration and therefore the response of the biosensor.

Techniques are commonly used to limit the diffusion of a sample during its transfer to a fluid cell. In particular, it is known to place, on either side of the sample, a fluid bubble, generally air, non-miscible with the sample or with the solution circulating before and after the sample. The sample is inserted into or surrounded by an air bubble upstream and an air bubble downstream of the fluid cell. Each air bubble separates the sample from a reference liquid that circulates in the fluid cell before and after the passage of the sample.

Thus, patent document JP2006-242912 describes a fluid transfer system capable of providing a long reaction duration, even for a small quantity of sample. In particular, JP2006-242912 describes a fluid system configured for recirculation of the sample in a closed circuit, the outlet of the fluid cell being connected to the inlet by means of a valve. In another alternative, JP2006-242912 describes a fluid system configured to generate a two-way passage of the sample in the fluid cell. In these two configurations, the sample to be analyzed is also separated from a buffer solution by means of an air bubble, in order to prevent any mixing between the sample and the buffer solution. In these devices, the air bubbles circulate inside a passage in the form of a channel and serve, for example, to trigger the reversal of the direction of circulation in a two-way movement.

In the fluid cell, the sample is analyzed by means of an optical analysis technique based, non-exhaustively, on evanescent optical phenomena such as, for example, SPR, but also other types of plasmons such as localized plasmons (LSPR) or long-range plasmons (LRSPR), resonant mirrors or Bloch surface waves (BSW).

In document JP2006-242912, which refers to the patent document JP3294605 for the structure of the SPR measurement equipment, the fluid analysis cell has a channel shape, which has a shape ratio, defined as the ratio between the width and the height, close to 1, the width being taken in the plane of the interaction surface, or functionalized surface, of the fluid cell and in the transverse direction of the fluid cell, and the height of the fluid cell being taken in a direction transversal to the plane of the interaction surface of the fluid cell. This channel may be likened to a tube. However, a channel is not suitable for containing a biochip. In this document, the fluid system is used both for functionalization of the channel, i.e. immobilization of the recognition probe molecules and for injection of the sample intended to be possibly recognized by the probe molecules. The arrival of an air bubble in a channel does not present a problem because this bubble fills the entire cross-section of the channel and the reference liquid pushes this bubble to the outlet. In addition, the functionalization of the channel being performed via the fluid system, enables homogeneous functionalization of the entire channel and therefore a constant hydrophobicity and/or hydrophilicity. There is therefore no area capable of trapping a bubble in this channel.

However, a fluid cell is configured so as to enable to immobilize a plurality, even several tens, or even several hundreds of ligands or recognition elements or different probes. To this end, the fluid analysis cell generally has an enlarged shape and has a shape factor well above 1, with, for example, a width of several millimeters and a height of several tens of microns. This type of fluid analysis cell with an enlarged cross-section is commonly used in devices enabling imaging of a biochip comprised of a matrix of plots (microarray), each plot being capable of containing a different probe molecule immobilized on said chip.

As an example, patent document US 2011/0052446_A1 describes different fluid cells coupled to fluid injection and extraction means.

In the remainder of this document, we will designate, by channel, a fluid analysis cell having a shape factor ~1 and, by fluid cell, only the fluid analysis cells having a shape factor >>1.

In the use of a fluid cell, the circulating fluid (liquid or gas) will pass over the biochip and therefore be in contact with, according to the locations of the biochip, the surface chemistry of one or the other of the different immobilized probe molecules. These different chemical and/or biological compounds immobilized on the surface have different hydrophobicities. Thus, a preferred direction of passage of an air bubble in the fluid cell is formed. Areas capable of trapping a portion of the air bubble in the fluid cell may also form.

For example, patent WO2012/045325 describes an SPR (surface plasmon resonance) measurement system and more specifically the placement of a two-way passage in the fluid system in order to increase the reaction time without increasing the consumption of reagents. WO2012/045325 mentions that, in order to perform this two-way passage, it is essential to separate the buffer solution from the sample by a fluid having a very different refraction index, such as a non-miscible liquid or a gas such as air. This separation prevents sample and buffer from mixing by diffusion. According to this document WO2012/045325, the passage of an air bubble into the fluid cell is used to trigger the start and end of the measurement of the sample by detection of a sudden shift in resonance induced by the sudden jump in the refraction index between the liquid medium and the air bubble.

However, an air bubble is capable of adhering to the sensitive surface of a sensor in a fluid cell and of modifying its surface properties, in particular when a hydrophobic layer is deposited on the sensor (see Handbook of Surface Plasmon Resonance, chapter 3.3.1, page 46).

It is known to use an in-line degasser to prevent the formation of bubbles, by degassing the sample or buffer solution in the fluid cell.

It therefore also appears to be important to prevent an air bubble used to separate the sample from the buffer solution from being trapped inside a fluid cell.

Thus, patent document WO03/025547 describes a system and a method enabling a sample to be analyzed by surface plasmon resonance in a microfluid cell, and proposes capillaries and areas for trapping an air bubble separating the sample from the buffer solution before the air bubble enters the fluid cell. More specifically, the device comprises a fluid circuit for bringing the sample in solution to at least one reaction chamber in order to react with one or more reagents. The fluid circuit comprises one or more vents for removing air bubbles from the fluid cell or the fluid circuit upstream of the fluid cell.

However, this device enables the sample to be circulated only in one direction, and does not enable two-way passages of the sample in the analysis chamber of the fluid cell.

There is therefore a need for a system and a method enabling the interaction duration of a fluid sample in a fluid cell to be increased, while preventing the diffusion between the fluid sample and a circulation fluid, such as a buffer solution, and preventing the interaction surface of the fluid cell from being modified due to the passage and/or trapping of an air bubble in the fluid cell.

This invention therefore proposes solving the problem of increasing the passage time of a sample in a fluid cell, in particular having a shape factor well above 1, compatible with different sample volumes, without increasing consumption, and while minimizing diffusion of the sample to other liquids, such as a buffer solution, during the passage of said sample in the fluid circuit, and while preventing an interaction surface of the fluid cell from being modified during the passage of a separation fluid, for example and air bubble, in the fluid cell.

OBJECT OF THE INVENTION

This invention is intended to overcome the disadvantages of the previous systems and more specifically proposes a system for transferring a fluid sample in a fluid cell, the fluid system comprising a fluid cell having a first inlet-outlet arranged upstream of said fluid cell and a second inlet-outlet arranged downstream of said fluid cell, a first fluid circuit connected to said first inlet-outlet and a second fluid circuit connected to said second inlet-outlet, first injection means connected to the first fluid circuit, said first injection means being configured so as to inject, in series, in the first fluid circuit: a buffer solution, a first separation fluid volume followed by a fluid sample then a second separation fluid volume and another buffer solution, and circulation means configured so as to circulate said fluid sample inserted between the first separation fluid volume and the second separation fluid volume in the first fluid circuit toward the first inlet-outlet of the fluid cell.

According to the invention, the system comprises first discharge means arranged on the first fluid circuit near the first inlet-outlet, said first discharge means being configured so as to extract, upstream of the fluid cell, said first separation fluid volume and, respectively, said second separation fluid volume, second injection means arranged on the second fluid circuit near the second inlet-outlet, said second injection means being configured so as to inject, downstream of the fluid cell, a third separation fluid volume between said buffer solution and the fluid sample and, respectively, a fourth separation fluid volume between the fluid sample and said other buffer solution, and two-way circulation means configured so as to circulate the fluid sample in a first direction of circulation going from said first inlet-outlet to said second inlet-outlet or in a second direction of circulation from said second inlet-outlet to said first inlet-outlet, without passage of the first, second, third or fourth separation fluid volume into said fluid cell.

The system of the invention, integrated on either side of the fluid cell, makes it possible to transfer a fluid sample, discharge the first separation bubble preceding the sample before it enters the fluid cell and to reinject a new separation bubble just after the outlet of the sample downstream of the fluid cell.

This system may be used in the same way to remove and reinject the second air bubble following the sample. Thus, each end of the sample is in contact with the buffer solution only for the duration of a passage through the fluid circuit, between the first discharge means and the second injection means, of a separation bubble, regardless of the length of the fluid circuit upstream of the fluid cell and regardless of the total duration of the passage of the sample into the fluid cell.

The duration of contact between the sample and the buffer solution and the diffusion induced are shorter inasmuch as the first discharge means and the second injection means are located as close as possible to the fluid cell. Nevertheless, this duration remains slightly longer than the duration of the passage of the sample through the fluid cell.

The system and the method of the invention enable a two-way circulation of the sample in the fluid cell for the time necessary for the interaction with a sensitive surface of a sensor, while introducing minimal diffusion and therefore dilution of the sample.

Advantageously, the system comprises an optical analysis device coupled to the fluid cell and configured so as to enable an optical analysis, for example of the SPR or LSPR type, of the sample in the fluid cell, or of an interaction between the sample and the sensitive surface of a sensor.

According to a first embodiment, the first discharge means include a first valve having at least one first inlet-outlet port fluidly connected to the first inlet-outlet of the fluid cell, a second inlet-outlet port fluidly connected to the first injection means, and a third inlet-outlet port, said first valve having at least one first state, in which the first inlet-outlet port of the first valve is connected to the second inlet-outlet port of the first valve and a second state, in which the second inlet-outlet port of the first valve is connected to the third inlet-outlet port of the first valve.

According to a particular aspect of the first embodiment, the second separation fluid injection means include a second valve having at least one first inlet-outlet port fluidly connected to the second inlet-outlet of the fluid cell, a second inlet-outlet port and a third inlet-outlet port fluidly connected to a separation fluid source, the second valve having at least one first state, in which the first inlet-outlet port of the second valve is connected to the second inlet-outlet port of the second valve and a second state, in which the second inlet-outlet port of the second valve is connected to the third inlet-outlet port of the second valve.

According to a second embodiment, the first separation fluid discharge means and the second separation fluid injection means include a valve having at least one first inlet-outlet port fluidly connected to the first inlet-outlet of the fluid cell, a second inlet-outlet port fluidly connected to the second inlet-outlet of the fluid cell, a third inlet-outlet port connected to the first injection means, a fourth inlet-outlet port fluidly connected to a separation fluid source, a fifth inlet-outlet port and a sixth inlet-outlet port, said fifth and sixth inlet-outlet ports preferably being fluidly connected to a discharge or recovery device, said valve having at least one first state in which the first inlet-outlet port is connected to the third inlet-outlet port and in which the second inlet-outlet port is connected to the sixth inlet-outlet port, said valve having at least one second state in which the third inlet-outlet port is connected to the fifth inlet-outlet port and/or in which the fourth inlet-outlet port is connected to the sixth inlet-outlet port.

According to a first variant of the system of the invention, the system includes a detector arranged on the first fluid circuit between the first injection means and the first separation fluid discharge means, the detector being configured so as to detect the first separation fluid volume and/or the second separation fluid volume.

Advantageously, the detector is configured so as to trigger a signal for detection of the first separation fluid and the second separation fluid, respectively, and also including a counter configured so as to calculate, on the basis of the signal for detection of the first separation fluid and the second separation fluid, respectively, a triggering signal of the second injection means in order to inject the third separation fluid volume between said buffer solution and the fluid sample and the fourth separation fluid volume between the fluid sample and said other buffer solution, respectively.

According to a particular aspect of the invention, the third separation fluid volume being an air volume, the second separation fluid injection means include an air pump preferably connected to an air filter, the third and fourth separation fluid volume being a volume of air.

According to a particular and advantageous aspect of the invention, the fluid cell has a ratio between width and height of the fluid analysis cell or a shape ratio greater than the shape ratio of the first and, respectively, the second fluid circuit.

Particularly advantageously, the fluid cell comprises a biochip configured for analysis of the fluid sample at least at one analysis site, and preferably in a matrix of analysis sites, the analysis preferably being an optical analysis, for example surface plasmon resonance (SPR), localized surface plasmon resonance (LSPR), resonant mirror, Bloch surface wave (BSW), integrated waveguide or resonant microcavities (WGM).

According to a particular and advantageous aspect of the invention, the system comprises synchronization means configured so as to synchronize the operation of the first separation fluid discharge means, second separation fluid injection means and two-way circulation means.

Advantageously, the fluid system also comprises a tank configured to receive the fluid(s) coming from the second inlet-outlet of the fluid cell.

The invention also concerns a method for transferring a fluid sample in a fluid system, the method comprising the following steps:
- injection, in series in a first fluid circuit, of a buffer solution followed by a first separation fluid volume, a fluid sample, then a second separation fluid volume and another buffer solution,
- circulation of the fluid sample inserted between the first separation fluid volume and the second separation fluid volume in the first fluid circuit toward the first inlet-outlet of the fluid cell,
- discharge, near the first inlet-outlet, of the first separation fluid volume, upstream of the fluid cell,
- passage of the buffer solution followed by the fluid sample into the fluid cell;
- injection, near the second inlet-outlet, of a third separation fluid volume between said buffer solution and the fluid sample downstream of the fluid cell, and
- two-way circulation of the fluid sample inserted between the second separation fluid volume and the third separation fluid volume, in a first direction of circulation going from said first inlet-outlet to said second inlet-outlet and/or in a second direction of circulation going from said second inlet-outlet to said first inlet-outlet without passage of the second or the third separation fluid volume into said fluid cell;
- discharge, near the first inlet-outlet, of the second separation fluid volume, upstream of the fluid cell,
- passage of the fluid sample into the fluid cell followed by the other buffer solution through the fluid cell from the first inlet-outlet toward the second inlet-outlet;
- injection, near the second inlet-outlet, of a fourth separation fluid volume between the fluid sample and the other buffer solution downstream of the fluid cell.

According to a particular and advantageous aspect, the method for transferring a fluid sample in a fluid system also includes the following steps:
- detection, upstream of the fluid cell, of the first separation fluid volume;
- triggering, on the basis of the signal for detection of the first separation fluid volume, of a counter configured to calculate a triggering signal of the second injection means so as to inject the third separation fluid volume between said buffer solution and the fluid sample downstream of the fluid cell.

According to another particular and advantageous aspect, the method for transferring a fluid sample in a fluid system also includes the following steps:
- detection, upstream of the fluid cell, of the second separation fluid volume;
- triggering, on the basis of the signal for detection of the second separation fluid volume, of a counter configured to calculate a triggering signal of the second injection means so as to inject the fourth separation fluid volume between the fluid sample and said other buffer solution downstream of the fluid cell.

This invention also concerns the features indicated in the following description and which should be considered separately or according to all technically possible combinations thereof.

Figure 7:
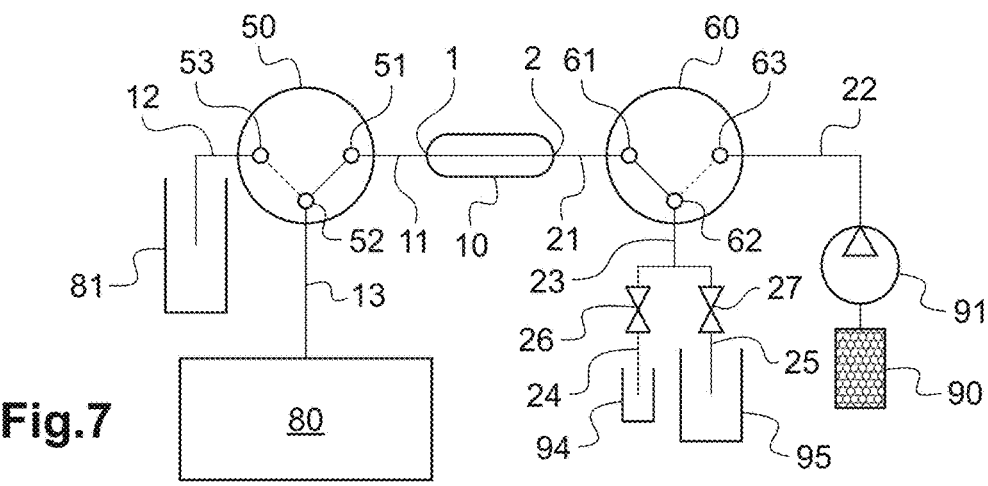
Figure 8:
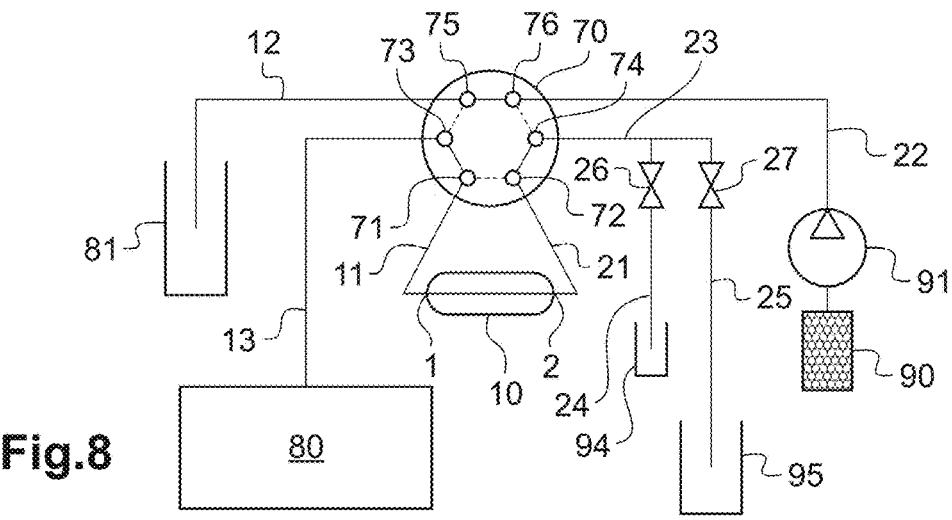
Figure 9:
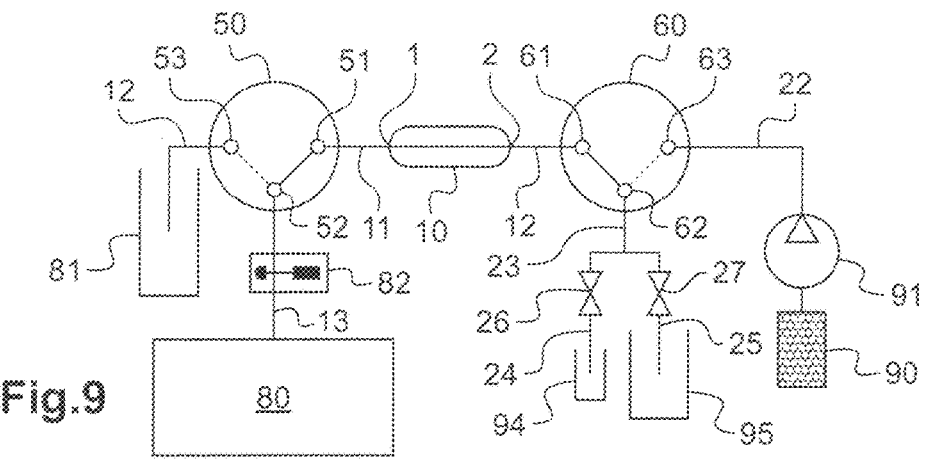
Figure 10:
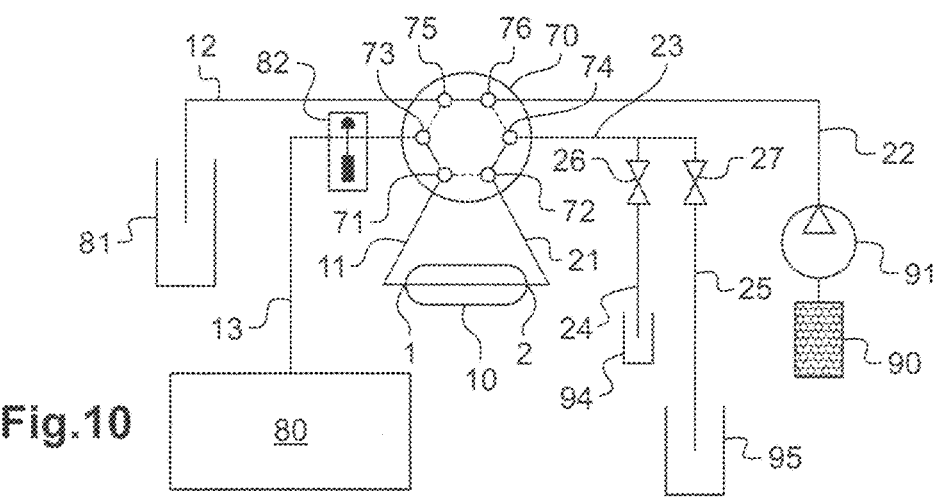
Figure 11:
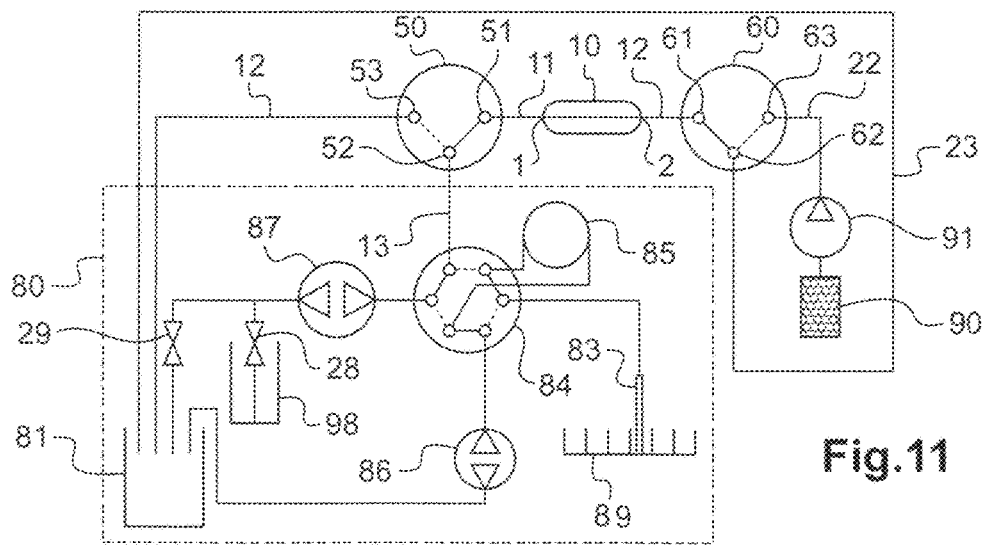

This description, provided by way of a non-limiting example, will make it easier to understand how the invention may be produced in reference to the following drawings:

FIGS. 1A-1F schematically show the main steps of an example of the transfer method according to the invention;

FIG. 2 shows an example of a digital kinetics simulation of the interaction of a sample with a recognition element immobilized on the chip and directed against one of the constituents of the sample;

FIGS. 3A-3C schematically show a system for transferring a fluid sample according to the first embodiment of the invention;

FIGS. 4A-4B schematically show a system for transferring a fluid sample according to a second embodiment of the invention;

FIG. 5 schematically shows a first variant of a system for transferring a fluid sample according to a first embodiment of the invention;

FIG. 6 schematically shows a first variant of a system for transferring a fluid sample according to the second embodiment of the invention;

FIG. 7 schematically shows a second variant of a system for transferring a fluid sample according to the first embodiment of the invention;

FIG. 8 schematically shows a second variant of a system for transferring a fluid sample according to the second embodiment of the invention;

FIG. 9 schematically shows a third variant of a system for transferring a fluid sample according to the second embodiment of the invention;

FIG. 10 schematically shows a third variant of a system for transferring a fluid sample according to the second embodiment of the invention;

FIG. 11 schematically shows a complete system for transferring a fluid sample according to an embodiment of the invention.

FIGS. 1A-1F schematically show the principle of a system according to an embodiment of the invention and the main steps of the transfer method.

SYSTEMS AND METHODS

FIGS. 1-A to 1-F show a fluid cell 10 intended to receive a sample in liquid form or dispersed in solution, to be analyzed. FIGS. 1-A to 1-F schematically show a fluid cell 10 from a top view. In the plane of FIGS. 1-A to 1-F, this fluid cell 10 has a general hexagonal, or square, or rectangular, or other shape. In a transverse plane with respect to the plane of FIGS. 1-A to 1-F, the fluid cell 10 has a cross-section with a rectangular and elongate shape. The fluid cell 10 comprises a first inlet-outlet 1 arranged upstream of the fluid cell 10 and a second inlet-outlet 2 arranged downstream of said fluid cell 10. The two inlets-outlets 1, 2 are, for example, arranged at the opposite apexes of a hexagon. The first inlet-outlet 1 is fluidly connected to a first fluid circuit, two branches 12 and 13 of which have been shown. Similarly, the second inlet-outlet 2 is fluidly connected to a second fluid circuit, two branches 22 and 23 of which have been shown. Branches 12 and 13 are for example formed by metal or polymer material tubes.

The fluid cell 10 is generally coupled to an analysis system, for example, an optical analysis system of the SPR, LSPR, LRSPR or BSW type. Advantageously, the fluid cell is in the form of a basin, suitable for receiving a fluid sample. For example, the fluid cell may be closed tightly by an optical coupling interface on which an optical beam is incident, so as to measure the interactions between said optical beam and the fluid sample. In a particularly advantageous manner, the optical coupling interface comprises a biosensor or a biochip on the surface in contact with the fluid sample. A biochip generally comprises different molecules immobilized on a surface and arranged in a matrix. To enable a large quantity of different ligands, or recognition elements or probes to be immobilized, the fluid cell 10 preferably has a shape factor >>1, typically with a width of several millimeters and a height of several tens of microns.

Generally, an injection and circulation system, such as an auto-injector, described in detail in reference to FIG. 11, takes a fluid sample 30 and injects it into a branch 13 of the first fluid circuit. The injection and circulation system move the fluid sample forward until it is in the fluid cell, where it interacts with a surface so as to be analyzed. The fluid sample 30 is then transferred to the second fluid circuit so as to be discharged or collected. The direction of circulation in the fluid circuit is indicated by an arrow in FIGS. 1A, 1-B, 1-C, 1-E and 1-F. To illustrate a two-way circulation, two arrows of opposite directions are shown in FIG. 1-D.

In general, the auto-injector first circulates a reference liquid 35, or a buffer solution, generally containing a solvent, such as water, or water and salts, for example PBS or HBS, through the fluid circuit 13, 23 and the fluid cell 10. Unlike the fluid sample 30 to be analyzed via the biosensor, the buffer solution 35 does not contain target molecules. The buffer solution 35 makes it possible to keep the fluid circuit 13, 23 and the fluid cell 10 clean, and prevents any contamination of the biosensor before the fluid sample 30 enters the fluid cell 10. The signal measured during passage of the buffer solution 35, before the sample, serves as a reference signal. The signal measured during the passage of the buffer solution 36 after the sample serves to measure the dissociation, i.e. the rate of separation between the probes and the targets.

To prevent dilution of the fluid sample 30 in a buffer solution 35 during its transfer to the fluid cell 10, the auto-injector inserts, just before and just after the fluid sample 30, a separation fluid bubble. The separation fluid is selected so as to be non-miscible with the fluid sample 30 or with the buffer solution. The separation fluid is generally air or an inert gas such as nitrogen or argon.

Thus, FIG. 1-A shows the passage of a buffer solution 35 through the fluid cell 10, from the first inlet-outlet 1 to the second inlet-outlet 2, toward the branch 23 of the second fluid circuit. A first air bubble 31 separates the buffer solution 35 from the sample 30. The first air bubble 31 and the fluid sample 30 circulate in the branch 13 of the first fluid circuit toward the first inlet-outlet of the fluid cell 10. A second air bubble 32 separates the sample 30 from the buffer solution 36 injected after the sample into the first fluid circuit (see FIGS. 1-C and 1-D). Thus, the sample 30 circulates in the branch 13 of the first fluid circuit upstream of the fluid cell 10, the sample 30 being inserted between the first air bubble 31 and the second air bubble 32.

In FIG. 1-A, the branch 12 of the first fluid circuit and, respectively, the branch 22 of the second fluid circuit are hermetically closed by a valve 41 and 42, respectively.

The sample 30 preceded by the first air bubble 31 is injected to near the first inlet-outlet 1 of the fluid cell 10.

In FIG. 1-B, the valve 41 on the branch 12 of the first fluid circuit is open and a valve 43 hermetically closes the circuit between the branch 13 and the first inlet-outlet 1 of the fluid cell 10. The auto-injector induces a circulation of the first air bubble 31 toward the branch 12 of the first fluid circuit. In the fluid cell 10, the circulation of buffer solution 35 is stopped. Thus, the first air bubble 31 is discharged before entering the fluid cell 10. In fact, an air bubble entering the fluid cell 10 is capable of attaching to and modifying the contact interface between the sample to be analyzed 30 and the interaction surface, for example of a biosensor. In addition, it is generally difficult to discharge an air bubble trapped in the fluid cell 10. Once the first air bubble 31 is extracted via the branch 12 of the first fluid circuit, the valve 41 is closed (see FIG. 1-C) and the valve 43 is opened again, so as to limit a loss of volume of the fluid sample 30 to be analyzed. The auto-injector then induces a circulation of the fluid sample 30 toward the fluid cell.

During the injection of the fluid sample 30 from the first inlet-outlet 1 to the second inlet-outlet, no separation fluid separates the fluid sample 30 from the buffer solution 35, which has already passed through the fluid cell. However, this step without separation fluid is limited to the duration of one passage of the sample into the cell 10 and the resulting dilution of the sample is generally very low.

In FIG. 1-C, the buffer solution 35 is discharged from the fluid cell 10 and the sample 30 reaches the second inlet-outlet 2 of the fluid cell 10. A valve 44 near the second inlet-outlet 2 is closed and a valve 42 is opened on a branch 22 of the second fluid circuit. In the fluid cell 10, the circulation of the sample 30 is stopped. A new air bubble 33 is inserted at the interface between the sample 30 and the buffer solution 35. The new air bubble 33 is inserted outside the fluid cell 10. The injection system induces a circulation of the new air bubble 33 and the buffer solution 35 to the branch 23 of the second fluid circuit. A second air bubble 32 separates the sample 30 from another separation fluid 36, which is generally of the same nature as the first separation fluid 35. The second air bubble 32 and the other separation fluid 36 are located on the branch 13 of the first fluid circuit upstream of the first inlet-outlet 1 of the fluid cell 10.

Thus, FIG. 1-D shows a fluid sample 30 that fills the fluid cell 10, the fluid sample 30 being inserted between two air bubbles 33, 32, separating it from the buffer solution 35, 36, without any air bubble having been injected into the fluid cell 10. An air bubble 32 is located on the branch 13 of the first fluid circuit upstream of the first inlet-outlet 1 of the fluid cell 10. And another air bubble 33 is located on the branch 23 of the second fluid circuit downstream of the first inlet-outlet 1 of the fluid cell 10. Advantageously, the auto-injector induces an alternating two-way circulation of the sample 30 in the fluid cell 10, the air bubbles 32, 33 surrounding the sample remaining outside of the fluid cell 10.

Preferably, the fluid sample 30 has a volume greater than the internal volume of the fluid cell 10. The volume of the fluid sample is determined so that the movement of the sample induced by a two-way movement is interrupted before the air bubble 32 enters via the first inlet-outlet 1 and before the air bubble 33 enters via the second inlet-outlet 2.

The two-way circulation enables the interaction time and the probability of interaction between the fluid sample 30 and the surface of a biosensor in the fluid cell to be increased.

During the two-way circulation, the sample is separated from the buffer solution 35, 36 at its two ends, enabling any dilution of the sample during the two-way passage to be avoided.

FIGS. 1-E and 1-F show the extraction of the sample 30 from the fluid cell 10. The auto-injector induces a circulation of the sample 30 from the first inlet-outlet 1 to the second inlet-outlet 2 of the fluid cell 10. When the air bubble 32, which separates the sample from the buffer solution 36 in the first fluid circuit, approaches the first inlet-outlet 1 of the fluid cell 10, the valve 43 is closed and the valve 41 is opened toward branch 12. The auto-injector thus pushes the air bubble 32 toward the branch 12 of the first fluid circuit. Thus, the air bubble 32 is discharged before entering the fluid cell 10. In the fluid cell 10, the circulation of the sample 30 is stopped.

Once the air bubble 32 is extracted via the branch 12 of the first fluid circuit, the valve 41 is closed and the valve 43 is opened. The auto-injector again induces a circulation of the fluid sample 30 and the buffer solution 36 through the fluid cell 10 from the inlet-outlet 1 to the inlet-outlet 2.

During extraction of the fluid sample 30 from the fluid cell, after discharge of the air bubble 32, no separation fluid separates the fluid sample 30 from the buffer solution 36. However, this step is limited to the duration of one passage of the sample in the cell 10 and the resulting dilution of the sample is generally very low.

In FIG. 1-F, the sample 30 is extracted from the fluid cell 10 and the buffer solution 36 reaches the second inlet-outlet 2 of the fluid cell 10. The valve 44 is closed near the second inlet-outlet 2 and the valve 42 is opened on branch 22 of the second fluid circuit. In the fluid cell 10, the circulation of buffer solution 36 is stopped. A new air bubble 34 is inserted at the interface between the sample 30 and the buffer solution 36. Thus, an air bubble 34 separates the sample 30 from the separation fluid 36, this new air bubble 34 being inserted outside the fluid cell 10. The injection system induces circulation of the new air bubble 34 and the sample 30 toward the branch 23 of the second fluid circuit. The air bubble 34 is injected on the branch 23 of the second fluid circuit downstream of the second inlet-outlet 2 of the fluid cell 10. In the second fluid circuit, the sample 30 therefore circulates again surrounded by two air bubbles 33, 34. The sample 30 may then be collected for other analyses, without having been significantly diluted in the buffer solution 35 or 36.

Thus, during steps 1-A to 1-F, none of the separation bubbles 31, 32, 33, 34 has been injected into the fluid cell 30. Nevertheless for the entire two-way circulation step, the system and the method enable a two-way circulation of the sample 30 in the fluid cell, the sample remaining separated from the buffer solution 35, 36 by an air bubble 32, 33 arranged respectively at each of its ends, as shown in FIG. 1-D.

In an example of use, the operator has only 500 µL, of a biological sample including a target molecule at a concentration of 500 pM. A biosensor is functionalized with a recognition molecule having an affinity Kd=50 nM with the target molecule ($k_a=1·10^4$ $M^{-1}s^{-1}$ and $k_d=5·10^{-4}$ $s^{-1}$). The interaction kinetics according to the simple stoichiometric model 1:1 generally follows a curve as indicated in FIG. 2, with a phase increasing as a function of time until equilibrium is reached. The decreasing phase of the curve in FIG. 2 corresponds to the dissociation phase: after the end of the sample has passed into the fluid cell (in this case at t=9000 s), the buffer solution 36 again circulates in the fluid cell. The analyte concentration therefore goes to 0, displacing the equilibrium. The molecules recognized will therefore progressively be detached at a more or less sustained rate.

In a system in which the circulation of the sample in the fluid cell is one-way, and for a circulation flow rate of 100 µL/min, the interaction time of the sample is then limited to a maximum of 300 s, which does not enable the equilibrium of the reaction to be reached, but only around 10% of the maximum value in FIG. 2.

By contrast, with the same sample and the system and method of the invention, a two-way circulation of the sample for some fifteen two-way passages in the fluid cell enables a total interaction time of 2 h30, and equilibrium of the reaction, to be reached. Thus, it is obtained a final response 10 times greater than with a fluid system in which the circulation is one-way, even though the total amount of available sample is extremely limited. For the 15 two-way passages, the sample remains separated from the buffer solution, preventing any dilution of the sample during these numerous two-way passages.

The system and the method described in relation with FIGS. 1-A to 1-F may be entirely automated.

FIGS. 3A-3C represent a system for transferring a fluid sample according to a first embodiment of the invention.

The system of FIGS. 3A-3C comprises an auto-injector 80, a fluid cell 10, an air pump 91 equipped with an air filter 90. The first inlet-outlet 1 of the fluid cell 10 is connected to a first branch 11 of the first fluid circuit. The second inlet-outlet 2 of the fluid cell 10 is connected to a first branch 21 of the second fluid circuit. A first valve 50 is arranged on the first fluid circuit near the first inlet-outlet 1. Advantageously, the first valve 50 comprises at least one inlet 52 and two outlets 51, 53. The inlet 52 of the first valve 50 is connected by a branch 13 to the auto-injector 80. The outlet 51 of the first valve 50 is connected by the branch 11 to the first inlet-outlet 1 of the fluid cell 10. The outlet 53 of the first valve 50 is connected by a branch 12 to a recipient 81, which serves, for example, as a waste collector. A second valve 60 is arranged on the second fluid circuit near the second inlet-outlet 2 of the fluid cell. Advantageously, the second valve 60 has at least two inlets 61, 63 and an outlet 62. The inlet 61 of the second valve 60 is connected by a branch 21 to the second inlet-outlet 2 of the fluid cell 10. The inlet 63 of the second valve 60 is connected by the branch 22 to the air pump 91. The outlet 62 of the second valve 60 is connected by a branch 23 to a recipient 93, which serves, for example, as a collector for recovering the sample after analysis or as a waste collector.

In FIG. 3-A, the inlet 52 and the outlet 51 of the first valve 50 are fluidly connected. The outlet 53 of the first valve 50 is not connected to the inlet 52, so the branch 12 is isolated from the first fluid circuit. In the second fluid circuit, the inlet 61 and the outlet 62 of the second valve 60 are fluidly connected. The inlet 63 of the second valve 60 is not connected to the outlet 62, so the branch 22 is isolated from the second fluid circuit. The auto-injector 80 makes it possible to inject, in an automated manner, into the branch 13 of the first fluid circuit, a sample surrounded by two air bubbles. The auto-injector 80 may then circulate the sample between two air bubbles in the direction going from the auto-injector 80 to the recipient 93 or in the opposite direction.

FIG. 3-A shows the step of injecting the sample into the fluid cell, or the step of two-way passage of the sample in the fluid cell, or the step of extraction of the sample from the fluid cell after analysis.

In FIG. 3-B, the first valve 50 has been switched, the second valve being in the same position as in FIG. 3-A. In the first fluid circuit, the inlet 52 and the outlet 53 of the first valve 50 are fluidly connected. The outlet 51 of the first valve 50 is not connected to the inlet 52, so the branch 11 is isolated from the first fluid circuit. The auto-injector 80 directs the fluid via branches 13 and 12 toward the recipient 81.

FIG. 3-B shows the configuration of a system for extracting an air bubble just before said bubble enters the fluid cell by the first inlet-outlet 1. FIG. 3-B shows the step of extraction of an air bubble 31, which precedes the sample to be analyzed, just before the sample 30 enters the fluid cell. FIG. 3-B also shows the step of extracting an air bubble 32 that follows the sample, during the step of extraction of the sample from the fluid cell.

In FIG. 3-C the first valve 50 and the second valve 60 have been switched with respect to FIG. 3-B. The first valve 50 is in the same position as in FIG. 3-A. In the second fluid circuit, the inlet 63 and the outlet 62 of the second valve 60 are fluidly connected. The inlet 61 of the second valve 60 is not connected to the outlet 62, so the branch 21 is isolated from the second fluid circuit. The air pump 91 induces fluid circulation via branches 22 and 23 toward recipient 93.

FIG. 3-C shows the configuration of a system for inserting an air bubble just after the second inlet-outlet 2 of the fluid cell. FIG. 3-C shows the step of injecting an air bubble 33 that precedes the sample to be analyzed, when the sample 30 is in the fluid cell 10. FIG. 3-C also shows the step of injecting an air bubble 34 that follows the sample, just after the step of extraction of the sample from the fluid cell.

A method for transferring a fluid sample in a system according to the first embodiment comprises the following steps:

a) the auto-injector 80 takes an air bubble 32, b) the auto-injector 80 takes the sample 30, c) the auto-injector 80 takes another air bubble 31, d) the auto-injector 80 injects, into the first fluid circuit, the sample 30 inserted between the two air bubbles 31, 32, for example, in the order 31-30-32, f the auto-injector moves the fluids in the first fluid circuit to the fluid cell 10 and toward the recipient 93, e) switching of the first valve 50 for discharge of bubbles toward the recipient 81, just before the arrival of the first bubble 31 at the first valve 50, f) discharging of the first bubble 31 toward the recipient 81, preferably with a safety margin, including a small amount of buffer solution 35 located just before the first bubble 31, the first bubble 31 and a small volume of sample 30 just after the first bubble 31, g) switching of the first valve 50 for discharging the bubbles toward the fluid cell 10, h) arrival of the start of the sample 30 in the fluid cell 10, i) switching of the second valve 60 for reinjection of the bubbles, just before the arrival of the start of the sample 30 at this second valve 60, which then passes from the fluid cell inlet 10 to the air pump inlet 91, j) starting of the air pump 91 in order to generate an air bubble 33 and injection of said air bubble 33 into the second fluid circuit between the second valve 60 and the recipient 93, k) switching of the second valve 60 for reinjection of the bubbles toward the second inlet-outlet of the fluid cell 10 so that the sample 30 is preceded by the bubble 33, l) reversal of the direction of circulation of the fluids in the fluid circuit just before the second bubble 32 arrives at the first bubble discharge valve 50, the sample 30 circulating in the direction of the recipient 93 toward the fluid cell 10 and the auto-injector 80;

m) reversal of the direction of circulation of the fluids in the fluid circuit, just before the arrival of the bubble 33 at the second bubble reinjection valve 60, the sample 30 then circulates in the direction of the auto-injector 80 toward the fluid cell 10 and the recipient 93;

n) repetition of the two previous steps as many times as necessary for reaching the required interaction time, i.e. the number of passages of the sample in the fluid cell, o) switching of the first bubble discharge valve 50, just before the arrival of the second bubble 32 at the first valve 50 toward the waste collector 81, p) discharge toward the waste collector 81 of the second bubble 32, preferably with a safety margin, including a small volume of sample 30 just before the bubble 32, the bubble 32 and a small amount of buffer solution 36 located just after the bubble 32, q) switching of the first bubble discharge valve 50 toward the fluid cell 10, r) end of passage of the sample 30 in the fluid cell 10, s) switching of the second bubble reinjection valve 60, just before the arrival of the end of the sample 30 at said valve 60, which then passes from the second inlet-outlet 2 of the fluid cell 10 to the air pump inlet 91, t) starting of the air pump 91 in order to generate an air bubble 34 and introduce it into the second fluid circuit between the bubble generating valve 60 and the recipient 93, u) switching of the second bubble reinjection valve 60 toward the second inlet-outlet 2 of the fluid cell 10 in order for the sample 30 to be followed by the bubble 34.

Alternatively, step j) is replaced by the following step:

j') starting of the air pump 91 in order to inject air into the fluid circuit between the second bubble generating valve and the recipient 93, which is equivalent to the generation of a bubble 33.

FIGS. 4A-4B show a fluid sample transfer system according to a second embodiment of the invention. The same elements are indicated by the same reference signs as in FIGS. 3A-3C. The first valve 50 and the second valve 60 are in this case replaced by a single valve 70 having six inlet-outlets 71, 72, 73, 74, 75, 76. The inlet-outlet 71 is fluidly connected by a branch 11 to the first inlet-outlet 1 of the fluid cell 10; the inlet-outlet 72 is fluidly connected by a branch 21 to the second inlet-outlet 2 of the fluid cell 10; the inlet-outlet 73 is fluidly connected by a branch 13 to the auto-injector 80; the inlet-outlet 75 is fluidly connected by a branch 12 to a collection recipient 81; the inlet-outlet 74 is fluidly connected by a branch 23 to another collection recipient 93; the inlet-outlet 76 is fluidly connected by a branch 22 to an air pump 91 and an air filter 90.

The valve 70 is preferably a valve with two states of operation.

FIG. 4-A shows the configuration of the system for transferring a fluid sample, the valve 70 being in a first state. In the first state, the inlet-outlet 73 is fluidly connected to the inlet-outlet 71. Thus, the fluid coming from the auto-injector 80, connected to the inlet-outlet 73, may be directed toward the inlet 1 of the fluid cell 10 connected to the inlet-outlet 71. In addition, in the first state, the inlet-outlet 72 is fluidly connected to the inlet-outlet 74. Thus, the fluid coming from the fluid cell 10, connected to the outlet 2 of the fluid cell 10, may be directed toward the collection recipient 93 connected to the inlet-outlet 74. FIG. 4A shows the fluid circuit in its main state, or first state, during the passage of the sample into the fluid cell 10. In this first state, the auto-injector 80 may push the sample toward the recipient 93 along the path formed by: the branch 13, the inlet-outlet 73, the inlet-outlet 71, the branch 11, the inlet-outlet 1, the fluid cell 10, the inlet-outlet 2, the branch 21, the inlet-outlet 72, the inlet-outlet 74 and the branch 23. In this first state, the auto-injector 80 may also aspirate the sample in the reverse direction. The auto-injector 80 can therefore pulse a circulation of the fluid sample in two directions.

The inlets-outlets 75 and 76 of the valve V 3 being connected, it is possible to send air to the recipient 81 along the path going from the air filter 90, via the pump 91, the branch 22, then to the inlet-outlet 76, the inlet-outlet 75, the branch 12, to the recipient 81. This sending of air directly to the recipient 81 does not constitute a step of the method of the invention. In the first state of the valve 70, it is preferable to turn off the air pump 91.

In summary, FIG. 4-A shows the operation of the system according to the second embodiment, during the step of injecting the sample into the fluid cell, during the step of discharging the sample from the fluid cell, or during a two-way circulation of the sample in the fluid cell.

FIG. 4-B shows the configuration of the fluid sample transfer system, the valve 70 being in a second state. In the second state, the inlet-outlet 73 is fluidly connected to the inlet-outlet 75. In the second state, the fluid coming from the auto-injector 80 may be directed toward the collection recipient 81 connected to the inlet-outlet 75 (FIG. 4-B). Thus, an air bubble 31, or 32, coming from the auto-injector 80, connected to the inlet-outlet 73, may be directed toward the collection recipient 81 connected to the inlet-outlet 75. In addition, in the second state, the inlet-outlet 74 is fluidly connected to the inlet-outlet 76. Thus, an air bubble 33, or 34, coming from the air pump 91, connected to the inlet-outlet 76, may be directed toward the branch 23 of the fluid circuit connected to the inlet-outlet 74. FIG. 4-B shows the operation of the system according to the second embodiment, during the step of extraction of an air bubble, upstream of the fluid cell or during the step of injection of an air bubble 33, or 34, downstream of the fluid cell.

FIG. 4B shows the fluid circuit in a second state which enables manipulation of bubbles around the fluid cell 10. In this second state, if we want to discharge an air bubble (31 or 32) upstream of the fluid cell 10, the auto-injector 80 may push the fluid and in particular an air bubble toward the recipient 81 along the path going from the branch 13, to the inlet-outlet 73, the inlet-outlet 75, the branch 12, to the recipient 81, while the air pump 91 is stopped so as not to inject other air bubbles in an undesirable manner. However, if we want to reinject an air bubble (33 or 34) downstream of the fluid cell 10, the air pump 91 may then be started. The air pump 91 aspirates air via the filter 90 and pushes the aspirated air toward the recipient 93 along the path going from the branch 22, to the inlet-outlet 76, the inlet-outlet 74, and the branch 23, toward the recipient 93, while the auto-injector 80 ceases pushing the fluids in order to avoid sending them directly to the recipient 81 without going through the fluid cell 10.

The second embodiment has the advantage of using a single valve instead of two valves and therefore of being more compact and less costly.

Thus, in the second embodiment, the valve 70 being in the second state, the inlet-outlet 71 is fluidly connected to the inlet-outlet 72. In a variant, by inserting an additional pump on branch 11 or 21, it is possible to circulate the sample in the fluid cell in a closed circuit, from the first inlet-outlet 1 of the fluid cell to the second inlet-outlet 2 of the fluid cell, passing through branches 11 and 12 and the inlet-outlets 71, 72 of the valve 70. The additional fluid circulation means are arranged so as to enable a one-way or two-way circulation movement to pulse the sample 30 in said recirculation loop.

FIG. 5 shows a first variant of the embodiment of the invention. The same elements are indicated by the same reference signs as in FIG. 3. The system of FIG. 5 also comprises a bubble detector 82 arranged on the branch 13 between the auto-injector 80 and the inlet-outlet 52 of the first valve 50 and preferably near the inlet-outlet 52. The auto-injector 80 injects, on branch 13 of the fluid circuit, a sample 30 inserted between a first air bubble 31 and a second air bubble 32. When the detector 82 detects the first bubble 31, which arrives at the detector 82 before the sample 30, the detector 82 triggers a signal for discharge of the first bubble 31. A control system causes the first valve 50 to switch in response to the discharge signal. According to one aspect of the invention, the switching time of the first valve 50 is determined by the quotient between the volume of the fluid circuit contained between the detector 82 and the inlet-outlet 52 of the valve 50 and the fluid circulation flow rate in the fluid circuit.

A person skilled in the art will use a bubble detector available on the market, for example an ultrasound detector or an optical detector.

When the detector 82 detects the second bubble 32, located after the sample, the detector 82 triggers a second bubble detection signal. This signal may be used to trigger either the discharge of the second bubble 32, similarly to the first bubble, or a change in direction of circulation during the two-way passage.

Advantageously, the detection of the first bubble 31 triggers a time counter. A calculator makes it possible to calculate, as a function of the volume of the fluid cell and the fluid circulation flow rate in the cell and/or as a function of an experimental measurement, the time at which a third air bubble 33 is reinjected downstream of the fluid cell. This third air bubble 33 serves to separate the fluid sample 30 from the buffer solution 35 that has already passed through the fluid cell. Thus, a counter and/or a calculator triggers the reinjection of the third air bubble 33.

Similarly, the detection of the second bubble 32 triggers a time counter, which makes it possible to calculate the time at which another air bubble 34 is reinjected downstream of the fluid cell, this other air bubble 34 being located at the interface between the sample 30 and the buffer solution 36, after the complete passage of the fluid sample 30 through the fluid cell 30. Thus, a counter and/or a calculator triggers the reinjection of the fourth air bubble 34.

According to the different variants, the time of reinjection of the bubble 33, 34, respectively, at the outlet of the fluid cell, is dependent upon the volume of the fluid sample, the volume of bubble injected and/or extracted, the direction of circulation in the fluid cell and/or the number of two-way passages in the cell. FIG. 6 shows a first variant of the second embodiment of the invention. The same elements are indicated by the same reference signs as in FIGS. 4A-4B. The system of FIG. 6 also comprises a bubble detector 82 arranged on the branch 13 between the auto-injector 80 and the inlet-outlet 73 of the valve 70 and preferably near the inlet-outlet 73.

The auto-injector 80 injects, on branch 13 of the fluid circuit, a sample 30 inserted between a first air bubble 31 and a second air bubble 32. When the detector 82 detects the first bubble 31, which arrives at the detector 82 before the sample 30, the detector 82 triggers a signal for discharge signal of the first bubble 31. A control system causes the valve 70 to switch from the first state to the second state, in response to the signal for discharge of the first bubble 31. Advantageously, the switching time of the valve 70 is determined by the quotient between the volume of the fluid circuit contained between the detector 82 and the inlet-outlet 73 of the valve 70 and the fluid circulation flow rate in the fluid circuit.

When the detector 82 detects the second bubble 32, located after the sample, the detector 82 triggers a signal for detection of a second bubble. This signal may be used to trigger either the discharge of the second bubble 32, similarly to the discharge of the first bubble, or a change in direction of circulation during the two-way passage.

FIG. 7 shows a second variant of a fluid sample transfer system according to the first embodiment of the invention. The same elements are indicated by the same reference signs as in FIG. 3A-3C. The system of FIG. 7 also comprises two additional valves 26, 27, arranged respectively on bifurcations 24, 25 of the branch 23 connected to the inlet-outlet 62 of the second valve 60. The additional valves 26, 27 make it possible to selectively orient the sample analyzed toward a recipient 94, for example a recovery tube, or toward another recipient 95, which serves for example as a waste collector. If it is desirable to remove the sample analyzed, the valve 26 is closed and the valve 27 is opened, so as to orient the fluid sample from the inlet-outlet 62 of the valve 60 to the branch 25, via the valve 27 and therefore toward the waste recipient 95. If it is desirable to recover the sample analyzed, the valve 26 is opened and valve 27 is closed, so as to orient the fluid sample from the inlet-outlet 62 of the valve 60 to the branch 24, via the valve 26 and therefore toward the recipient 94, for example a recovery tube.

FIG. 8 shows a second variant of a system for transferring a fluid sample according to the second embodiment of the invention. The same elements are indicated by the same reference signs as in FIGS. 4A-4B. The system of FIG. 8 also comprises two additional valves 26, 27 arranged respectively on bifurcations 24, 25 of the branch 23 connected to the inlet-outlet 71 of the valve 70. The additional valves 26, 27 make it possible to selectively orient the sample analyzed toward a recipient 94, for example a recovery tube, or toward another recipient 95, which serves for example as a waste collector. If it is desirable to remove the sample analyzed, the valve 26 is closed and the valve 27 is opened, so as to orient the fluid sample from the inlet-outlet 74 of the valve 70 to the branch 25, via the valve 27 and therefore toward the waste recipient 95. If it is desirable to recover the sample analyzed, the valve 26 is opened and valve 27 is closed, so as to orient the fluid sample from the inlet-outlet 74 of the valve 70 to the branch 24, via the valve 26 and therefore toward the recipient 94, for example a recovery tube.

FIG. 9 schematically shows a third variant of a fluid sample transfer system according to the first embodiment, which combines the first and second variants. The same elements are indicated by the same reference signs as in FIGS. 3A-3C, 5 and 7. The operation of the different elements is similar to that described in relation to FIGS. 3A-3C, 5 and 7.

FIG. 10 schematically shows a third variant of a fluid sample transfer system according to the second embodiment of the invention, which combines the first and second variants. The same elements are indicated by the same reference signs as in FIGS. 4A-4B, 6 and 8. The operation of the different elements is similar to that described in relation with FIGS. 4A-4B, 6 and 8.

FIG. 11 schematically shows a complete fluid sample transfer system according to an embodiment of the invention. An auto-injector 80 includes a source microplate 89 comprising wells, each well containing a sample to be analyzed. A needle 83 may be moved opposite each of the wells of the microplate 89. A two-state injection valve 84, connected to a loop 85, and a pump 86 make it possible to collect the samples in the microplate 89. Another pump 87 makes it possible to continuously circulate the fluids in the fluid detection circuit. The fluid detection circuit comprises the fluid cell 10, and two valves 28, 29, which make it possible to select a buffer solution tank 98 or a waste recipient 81. The auto-injector 80 has two main states according to the position of the valve 84, which is either in the position of loading a sample into the fluid circuit (as shown in FIG. 11), or in the position of injecting the sample toward the fluid cell 10 (not shown).

In the filling state, the pump 86 aspirates, via the needle 83, along the path starting from the needle 83, valve 84, loop 85, valve 84, toward the recipient 81. First, the pump 86 aspirates an air bubble of defined volume when the needle 83 is positioned outside of the microplate 89, then a predefined volume of sample when the needle 83 is positioned in a well of the microplate 89, and, finally, another air bubble. During this time, in the filling state, the pump 87 continuously aspirates a buffer solution from the tank 98, the valve 28 being open and the valve 29 being closed. The pump 87 causes the buffer solution to circulate toward the fluid cell 10.

In the injection state, during the to-way of the injection, the pump 87 may aspirate the circulation buffer fluid coming from the tank 98, the valve 28 being open and the valve 29 being closed. The pump 87 pushes the buffer fluid through the loop 85, which contains the sample surrounded by the bubbles, toward the fluid cell 10, along the path 98, 28, 87, 84, 85, 84, branch 13, valve 50, branch 11, inlet-outlet 1. The sample thus arrives progressively toward the fluid cell 10. During the fro-way of the injection, the pump 87 may aspirate the fluids coming from the fluid cell 10 and push them toward the waste recipient 81, the valve 28 being closed and the valve 29 being open, along the first branch 23, valve 60, branch 12, inlet-outlet 2, fluid cell 10, inlet-outlet 1, branch 11, valve 50, branch 13, valve 84, loop 85, valve 84 toward the waste recipient 81. The sample therefore progressively returns. The alternation between these to and fro directions during the injection state makes it possible to perform the two-way passage. During this time, the pump 86 is stopped.

The system and the method of the invention may be implemented on fluid analysis systems that already exist. The adaptation of an analysis system involves only minor modifications.

The invention claimed is:

1. A fluid system for transferring a fluid sample in a fluid cell, the fluid system comprising:
   a fluid cell having a first inlet-outlet arranged upstream of said fluid cell and a second inlet-outlet arranged downstream of said fluid cell;
   a first fluid circuit connected to said first inlet-outlet;
   a second fluid circuit connected to said second inlet-outlet;
   an auto-injector connected to the first fluid circuit, said auto-injector being configured so as to inject, in series, in the first fluid circuit: a buffer solution, a first separation fluid volume followed by a fluid sample, then a second separation fluid volume and another buffer solution,
   wherein said auto-injector is configured so as to circulate said fluid sample inserted between the first separation fluid volume and the second separation fluid volume in the first fluid circuit toward the first inlet-outlet of the fluid cell;
   a valve system arranged on the first fluid circuit and on the second fluid circuit, said valve system being configured so as to extract, upstream of the fluid cell, said first separation fluid volume and, respectively, said second separation fluid volume;

an air pump arranged on the second fluid circuit, said valve system and said air pump being configured so as to inject, downstream of the fluid cell, a third separation fluid volume between said buffer solution and the fluid sample and, respectively, a fourth separation fluid volume between the fluid sample and said another buffer solution; and a detector arranged on the first fluid circuit between the auto-injector and the valve system, the detector being configured to detect at least one of the first separation fluid volume or the second separation fluid volume, wherein the detector is configured to trigger a signal for detection of the first separation fluid and the second separation fluid, respectively, and the detector including a counter configured so as to calculate, on the basis of the signal for detection of the first separation fluid and the second separation fluid, respectively, a triggering signal of the air pump in order to inject the third separation fluid volume between said buffer solution and the fluid sample and the fourth separation fluid volume between the fluid sample and said another buffer solution, respectively, wherein the auto-injector is configured in alternating two-way circulation to circulate the fluid sample in a first direction of circulation going from said first inlet-outlet to said second inlet-outlet and, alternately, in a second direction of circulation from said second inlet-outlet to said first inlet-outlet, without passage of the first, second, third or fourth separation fluid volume into said fluid cell, and wherein the valve system includes a valve having at least one first inlet-outlet port fluidly connected to the first inlet-outlet of the fluid cell, a second inlet-outlet port fluidly connected to the second inlet-outlet of the fluid cell, a third inlet-outlet port connected to the auto-injector, a fourth inlet-outlet port fluidly connected to a separation fluid source, a fifth inlet-outlet port and a sixth inlet-outlet port, said fifth and sixth inlet-outlet ports being fluidly connected to a discharge or recovery device, said valve having at least one first state in which the first inlet-outlet port is connected to the third inlet-outlet port and in which the second inlet-outlet port is connected to the sixth inlet-outlet port, said valve having at least one second state in which the third inlet-outlet port is connected to the fifth inlet-outlet port and/or in which the fourth inlet-outlet port is connected to the sixth inlet-outlet port.

2. The fluid system for transferring a fluid sample in a fluid cell, according to claim 1, in which the fluid cell has a shape factor >1 or a shape ratio greater than the shape ratio of the first and the second fluid circuit.

3. The fluid system for transferring a fluid sample in a fluid cell, according to claim 1, further comprising a synchronization device configured to synchronize the operation of the valve system, air pump, and auto-injector.

4. A fluid system for transferring a fluid sample in a fluid cell, the fluid system comprising:

a fluid cell having a first inlet-outlet arranged upstream of said fluid cell and a second inlet-outlet arranged downstream of said fluid cell;

a first fluid circuit connected to said first inlet-outlet;

a second fluid circuit connected to said second inlet-outlet;

an auto-injector connected to the first fluid circuit, said auto-injector being configured so as to inject, in series, in the first fluid circuit: a buffer solution, a first separation fluid volume followed by a fluid sample then a second separation fluid volume and another buffer solution, wherein said auto-injector is configured so as to circulate said fluid sample inserted between the first separation fluid volume and the second separation fluid volume in the first fluid circuit toward the first inlet-outlet of the fluid cell;

a valve system arranged on the first fluid circuit and on the second fluid circuit, said valve system being configured so as to extract, upstream of the fluid cell, said first separation fluid volume and, respectively, said second separation fluid volume;

an air pump arranged on the second fluid circuit, said valve system and said air pump being configured so as to inject, downstream of the fluid cell, a third separation fluid volume between said buffer solution and the fluid sample and, respectively, a fourth separation fluid volume between the fluid sample and said another buffer solution; and a detector arranged on the first fluid circuit between the auto-injector and the valve system, the detector being configured so as to detect at least one of the first separation fluid volume or the second separation fluid volume, wherein the detector is configured to trigger a signal for detection of the first separation fluid and the second separation fluid, respectively, and the detector including a counter configured so as to calculate, on the basis of the signal for detection of the first separation fluid and the second separation fluid, respectively, a triggering signal of the air pump in order to inject the third separation fluid volume between said buffer solution and the fluid sample and the fourth separation fluid volume between the fluid sample and said another buffer solution, respectively, wherein the auto-injector is configured in alternating two-way circulation to circulate the fluid sample in a first direction of circulation going from said first inlet-outlet to said second inlet-outlet and, alternately, in a second direction of circulation from said second inlet-outlet to said first inlet-outlet, without passage of the first, second, third or fourth separation fluid volume into said fluid cell, and wherein the fluid cell comprises a biochip configured for analysis of the fluid sample at least at one analysis site, the analysis being an optical analysis selected among surface plasmon resonance (SPR), localized surface plasmon resonance (LSPR), resonant mirror, Bloch surface wave (BSW), integrated waveguide and resonant microcavities (WGM).

5. The fluid system for transferring a fluid sample in a fluid cell, according to claim 4, further comprising a synchronization device configured to synchronize the operation of the valve system, air pump, and auto-injector.

6. The fluid system for transferring a fluid sample in a fluid cell, according to claim 4, in which the fluid cell has a shape factor >1 or a shape ratio greater than the shape ratio of the first and the second fluid circuit.

7. A fluid system for transferring a fluid sample in a fluid cell, the fluid system comprising:

a fluid cell having a first inlet-outlet arranged upstream of said fluid cell and a second inlet-outlet arranged downstream of said fluid cell;

a first fluid circuit connected to said first inlet-outlet;

a second fluid circuit connected to said second inlet-outlet;

an auto-injector connected to the first fluid circuit, said auto-injector being configured so as to inject, in series, in the first fluid circuit: a buffer solution, a first separation fluid volume followed by a fluid sample then a second separation fluid volume and another buffer solution, wherein said auto-injector is configured so as to circulate said fluid sample inserted between the first separation fluid volume and the second separation fluid volume in the first fluid circuit toward the first inlet-outlet of the fluid cell;

a valve system arranged on the first fluid circuit and on the second fluid circuit, said valve system being configured so as to extract, upstream of the fluid cell, said first separation fluid volume and, respectively, said second separation fluid volume;

an air pump arranged on the second fluid circuit, said valve system and said air pump being configured so as to inject, downstream of the fluid cell, a third separation fluid volume between said buffer solution and the fluid sample and, respectively, a fourth separation fluid volume between the fluid sample and said another buffer solution;

a detector arranged on the first fluid circuit between the auto-injector and the valve system, the detector being configured so as to detect at least one of the first separation fluid volume or the second separation fluid volume, wherein the detector is configured to trigger a signal for detection of the first separation fluid and the second separation fluid, respectively, and the detector including a counter configured so as to calculate, on the basis of the signal for detection of the first separation fluid and the second separation fluid, respectively, a triggering signal of the air pump in order to inject the third separation fluid volume between said buffer solution and the fluid sample and the fourth separation fluid volume between the fluid sample and said another buffer solution, respectively, wherein the auto-injector is configured in alternating two-way circulation to circulate the fluid sample in a first direction of circulation going from said first inlet-outlet to said second inlet-outlet and, alternately, in a second direction of circulation from said second inlet-outlet to said first inlet-outlet, without passage of the first, second, third or fourth separation fluid volume into said fluid cell; and a tank configured to receive the fluid(s) coming from the second inlet-outlet of the fluid cell.

8. The fluid system for transferring a fluid sample in a fluid cell, according to claim 7, in which the fluid cell has a shape factor >1 or a shape ratio greater than the shape ratio of the first and the second fluid circuit.

9. The fluid system for transferring a fluid sample in a fluid cell, according to claim 7, further comprising a synchronization device configured to synchronize the operation of the valve system, air pump, and auto-injector.

* * * * *